(12) United States Patent
Janssen et al.

(10) Patent No.: US 8,188,296 B2
(45) Date of Patent: May 29, 2012

(54) GENTISIC ACID FOR STABILISING 123-I RADIOPHARMACEUTICALS

(75) Inventors: Ton Janssen, Eindhoven (NL); Jan Van Den Bos, Eindhoven (NL)

(73) Assignee: GE Healthcare Limited, Little Chalfont (GB)

( * ) Notice: Subject to any disclaimer, the term of this patent is extended or adjusted under 35 U.S.C. 154(b) by 896 days.

(21) Appl. No.: 11/995,222

(22) PCT Filed: Mar. 31, 2006

(86) PCT No.: PCT/GB2006/001215
§ 371 (c)(1),
(2), (4) Date: Jul. 14, 2008

(87) PCT Pub. No.: WO2007/007021
PCT Pub. Date: Jan. 18, 2007

(65) Prior Publication Data
US 2009/0005595 A1    Jan. 1, 2009

(30) Foreign Application Priority Data
Jul. 11, 2005 (GB) .................................. 0514087.6

(51) Int. Cl.
*C07D 207/32* (2006.01)
*C07C 279/04* (2006.01)
*A61K 51/04* (2006.01)
*A61K 47/12* (2006.01)
*A61K 9/08* (2006.01)

(52) U.S. Cl. ........ 548/401; 548/567; 562/473; 564/237; 514/428; 514/568; 514/634

(58) Field of Classification Search .................. None
See application file for complete search history.

(56) References Cited

U.S. PATENT DOCUMENTS

| 4,233,284 A | 11/1980 | Fawzi et al. |
| 4,497,744 A | 2/1985 | Fawzi et al. |
| 4,942,231 A | 7/1990 | Mertens |
| 5,384,113 A | 1/1995 | Deutsch et al. |
| 6,315,979 B1 | 11/2001 | Simon et al. |

FOREIGN PATENT DOCUMENTS

| EP | 0508724 | 8/1996 |
| WO | 93/04702 | 3/1993 |
| WO | 99/62564 | 12/1999 |
| WO | 02/04030 | 1/2002 |
| WO | 2005009393 | 2/2005 |
| WO | WO 2005/009393 | 2/2005 |

OTHER PUBLICATIONS

Mertens, J. "New fast preparation of 123-I labeled radiopharmaceuticals" Eur. J. Nucl. Med., 1987, vol. 13, pp. 380-381.
GB0514087.6 Search report dated Nov. 30, 2005.
PCT/GB2006/001215 Int'l Search Report/Written Opinion dated Jul. 19, 2006.
PCT/GB2006/001215 IPER Dated Jun. 12, 2007.
Maffioli, L, et al., "Scintigraphic Detection of Melanoma Metastases with a Radiolabeled Benzamide ([Iodine-123]—(S)-IBZM)", Journal of Nuclear Medicine, 35(11), (1994), 1741-1747.
Mertens, J., et al., "New Fast Preparation of 123I Labelled Radiopharmaceuticals", European Journal of Nuclear Medicine, 13, (1987), 380-381.

*Primary Examiner* — Brian J Davis

(57) ABSTRACT

The present invention relates to stabilized $^{123}$I-labelled radiopharmaceutical compositions having a stabilizer which comprises gentisic acid or a salt thereof with a biocompatible cation. Methods of preparation of the stabilized radioiodine compositions as well as the use of gentisic acid to stabilize $^{123}$I-labelled radiopharmaceutical at a specified radioactive concentration range are also described.

15 Claims, 1 Drawing Sheet

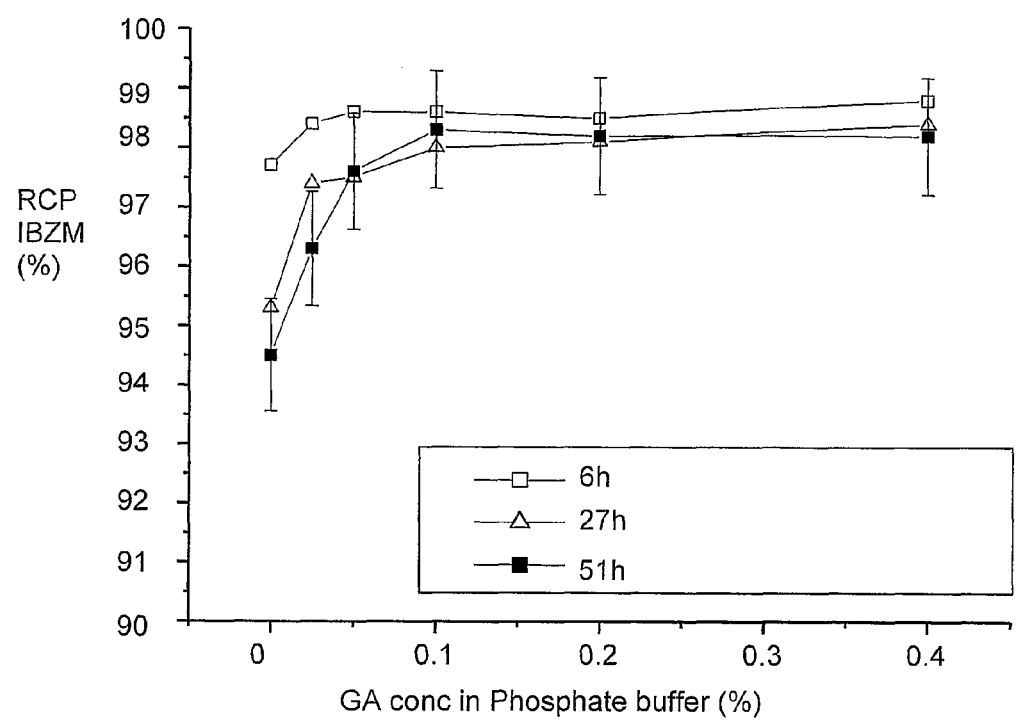
Effect of Concentration of Stabilisation of $^{123}$I-IBZM on Radiochemical Purity at Various Times post-Preparation.

GENTISIC ACID FOR STABILISING 123-I RADIOPHARMACEUTICALS

This application is a filing under 35 U.S.C. 371 of international application number PCT/GB2006/001215, filed Mar. 31, 2006, which claims priority to application number 0514087.6 filed Jul. 11, 2005, in Great Britain the entire disclosure of which is hereby incorporated by reference.

FIELD OF THE INVENTION

The present invention relates to stabilised $^{123}$I-labelled radiopharmaceutical compositions having a stabiliser which comprises gentisic acid or a salt thereof with a biocompatible cation.

BACKGROUND TO THE INVENTION

Gentisic acid has been disclosed as a stabiliser for use in lyophilised kits for the preparation of $^{99m}$Tc diphosphonic acid radiopharmaceuticals [Tofe et al, J. Nucl. Med., 21, 366-370 (1980)]. U.S. Pat. No. 4,233,284 and U.S. Pat. No. 4,497,744 disclose similar subject matter.

U.S. Pat. No. 5,384,113 discloses that gentisic acid, gentisyl alcohol and water soluble salts, esters and mixtures thereof are useful to prevent autoradiolysis of peptides radiolabelled with $^{111}$In, $^{67}$Ga, $^{169}$Yb, $^{125}$I, $^{123}$I or $^{201}$Tl. Examples 1 to 7 of U.S. Pat. No. 5,384,113 refer to $^{111}$In-labelled peptides, and Example 9 to a $^{186}$Re-labelled peptide. Example 8 describes the preparation of $^{123}$I-labelled LH-RH (luteinizing hormone releasing factor). Example 8 does not, however, does not include any evidence that gentisic acid is an effective stabiliser for $^{123}$I-LH-RH.

U.S. Pat. No. 6,315,979 discloses radioiodinated phenol derivatives of the formula shown for use as renal function imaging radiopharmaceuticals and in brachytherapy:
where: m and n are independently 0, 1, 2 or 3;

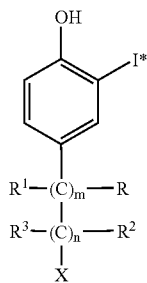

X is a group that is negatively or positively charged at physiological pH;
R, R$^1$, R$^2$ and R$^3$ are independently H or C$_{1-4}$ alkyl; and
I* is $^{123}$I, $^{131}$I or $^{125}$I.

U.S. Pat. No. 6,315,979 discloses that the radioiodinated phenols may potentially be stabilised with a variety of stabilisers chosen from: benzyl alcohol, ascorbic acid, gentisic acid, cysteine, butylated hydroxytoluene (BHT), citric acid, human serum albumin (HSA), glycerol, cysteamine, sulfarem, glutathione, tryptophan and iodoacetamide. No specific disclosure is made on the use of gentisic acid to stabilise radioiodinated phenols.

WO 02/04030 discloses pharmaceutical compositions comprising a radiolabelled pharmaceutical agent labelled with a radioisotope chosen from: $^{99m}$Tc, $^{131}$I, $^{125}$I, $^{123}$I, $^{117m}$Sn, $^{111}$In, $^{97}$Ru, $^{203}$Pb, $^{67}$Ga, $^{68}$Ga, $^{89}$Zr, $^{90}$Y, $^{177}$Lu, $^{149}$Pm, $^{153}$Sm, $^{166}$Ho, $^{32}$P, $^{211}$At, $^{47}$SC, $^{109}$Pd, $^{105}$Rh, $^{186}$Re, $^{188}$Re, $^{60}$Cu, $^{62}$Cu, $^{64}$Cu and $^{67}$Cu; stabilised with a compound of formula:

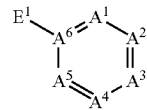

where E$^1$ is NH$_2$ or OH; A$^1$, A$^2$, A$^3$, A$^4$ and A$^5$ are each independently N, C(OH) or CR$^1$; provided that at least one of A$^1$, A$^2$, A$^3$, A$^4$ and A$^5$ is not CH; each R$^1$ is independently H, C(O)R$^2$, C(O)OR$^2$, NHC(=O)NHR$^2$, NHC(=S)NHR$^2$, OC(=O)R$^2$, OC(=O)OR$^2$, S(O)$_2$OR$^2$, C(O)NR$^3$R$^4$, C(O)NR$^3$OR$^4$, C(O)NR$^2$NR$^3$R$^4$, NR$^3$R$^4$, NR$^3$C(O)R$^4$, PO(OR$^3$)(OR$^4$), S(O)$_2$NR$^3$R$^4$, S(O)$_2$NR$^2$NR$^3$R$^4$, S(O)$_2$NR$^3$OR$^4$, C$_1$-C$_{10}$ alkyl substituted with 0-5 R$^5$, C$_3$-C$_{10}$ cycloalkyl substituted with 0-5 R$^5$, C$_2$-C$_{10}$ alkenyl substituted with 0-5 R$^5$, or aryl substituted with 0-5 R$^5$; R$^2$, R$^3$, and R$^4$ are each independently H, C$_1$-C$_6$ alkyl, C$_3$-C$_6$ cycloalkyl, C$_1$-C$_6$ alkenyl, benzyl, or phenyl; or R$^3$ and R$^4$ together form C$_3$-C$_{10}$ cycloalkyl or C$_3$-C$_{10}$ cycloalkenyl, optionally interrupted with O, S, NH, S(=O), S(O)$_2$, P(=O)(OH), C(=O)NH, NHC(=O), NH(C=O)NH, or NH(C=S)NH; and each R$^5$ is independently H, NH$_2$, OH, CO$_2$H, C(=O)NH$_2$, C(=O)NHOH, C(=O)NHNH$_2$, NH(C=NH)NH$_2$, NH(C=O)NH$_2$, NH(C=S)NH$_2$, PO$_3$H$_2$, SO$_3$H, or S(O)$_2$NH$_2$; or a pharmaceutically acceptable salt thereof.

WO 02/04030 does not seem to define A$^6$. The term "non-peptide" is defined very broadly to be a compound having less than 3 amide bonds in the backbone or less than 3 amino acids. The specification states that the stabiliser is preferably not gentisic acid. No specific disclosure is made on the use of gentisic acid as a stabiliser for radioiodine radiopharmaceuticals.

Mallinckrodt sell an $^{123}$I-labelled meta-iodobenzylguanidine radiopharmaceutical product [MIBG (I-123) Injection] which contains gentisic acid at a concentration of approximately 0.5 mg/ml. The pH of the preparation is 4.0±0.5.

Eersels et al [J. Lab. Comp. Radiopharm., 48, 241-257 (2005)], review methods of manufacturing $^{123}$I-labelled radiopharmaceuticals. At page 254 they mention that acidic conditions (pH 3-4 buffer) are advisable to minimise deiodination during autoclaving, but that for some compounds it is necessary to also employ a radical scavenger to suppress deiodination. Classical radical scavengers such as ascorbic acid or gentisic acid are said to be often omitted during autoclaving due to their colouration. The radical scavengers thiourea, N-acetylcysteine and ortho-iodohippuric acid (OIH) are said to give satisfactory results in stabilising a specific compound ($^{123}$I-R91150) against radiolysis, but of these only OIH was viewed as being suitable for use in a composition for intravenous human injection (pages 254-55).

THE PRESENT INVENTION

The generally accepted mechanism of deiodination of radioiodine radiopharmaceuticals in vitro is radiolysis of the imaging agent in aqueous solution. In aqueous media, radioactive decay causes the formation of highly-reactive oxygen species that react with organic molecules. The reactive species arise from degradation of the water solvent, and are free radicals such as hydroxyl or superoxide free radicals.

$^{123}$I has a half-life of 13.2 hours. Commercial $^{123}$I-labelled radiopharmaceuticals require time after the initial production to quality control, package and then distribute the agent to the hospital for patient use. The distribution and customer delivery may involve air freight, plus road journeys, so the elapsed time between point of manufacture and point of use may be approximately 24 hours. This is close to two half-lives for $^{123}$I. Consequently, the radioactive concentration (RAC) at the time of commercial manufacture must be significantly higher than that at point of use to allow for losses due to radioactive decay. A further consideration is that, for successful products, larger batch sizes and/or earlier production times become necessary, so that greater quantities of radioactivity and higher RAC must be used. These factors represent a significant increase in the risk of radiolysis.

The rate of deiodination of $^{123}$I-radiopharmaceuticals can often be suppressed in lower pH media (pH 3 or less), but is more rapid at higher pH (especially pH 7 or above). A radiopharmaceutical product for intravenous injection must, however, be formulated at a pH which is biocompatible, and does not cause discomfort on injection. Such products are therefore typically formulated at a pH in the range 4.5 to 8.5, so suppression of deiodination at higher RAC by the use of low pH media is not a viable option for radiopharmaceuticals. Certain radiopharmaceuticals may also be chemically unstable at alkaline pH—e.g. ester groups may hydrolyse at pH greater than 8. There is therefore a need for stabilised $^{123}$I-radiopharmaceuticals at a formulation pH which is appropriate for intravenous injection.

Although gentisic acid has been used previously as a stabiliser for $^{99m}$Tc radiopharmaceuticals, its use with $^{123}$I-labelled radiopharmaceuticals has been limited, probably due to the facts that it:

(a) discolours on standing in solution to give a brown colouration;
(b) discolours on heating in solution (i.e. as used in heat sterilisation processes) to give a brown colouration.

Such colourations are clearly highly undesirable for products intended for intravenous administration to patients.

The present invention provides gentisic acid stabilised $^{123}$I radiopharmaceutical compositions, plus methods of preparation of such compositions in which such discolouration problems are resolved.

BRIEF DESCRIPTION OF THE DRAWINGS

FIG. 1 shows the effect of concentration of gentisic acid stabilizer on the radiochemical purity of $^{123}$I-IBZM at various times post-preparation.

DETAILED DESCRIPTION OF THE INVENTION

In a first aspect, the present invention provides a stabilised radiopharmaceutical composition which comprises:
(i) a synthetic compound which targets a site within the mammalian body when administered in vivo which is labelled with $^{123}$I;
(ii) a stabiliser which comprises gentisic acid or a salt thereof with a biocompatible cation in an amount effective to stabilise said $^{123}$I-labelled synthetic compound against radiolysis;
(iii) an aqueous biocompatible carrier medium;
wherein the radioactive concentration of the $^{123}$I in the medium is in the range 8 to 1000 MBq/cm$^3$ and the pH of the biocompatible carrier medium is in the range 4.5 to 8.5;
with the proviso that when the synthetic compound which targets a site within the mammalian body is meta-iodobenzylguanidine, the pH of the biocompatible carrier medium is in the range 5.0 to 8.5.

The term "synthetic" has the conventional meaning of the term, i.e. man-made as opposed to being isolated from natural sources e.g. from the mammalian body. Such compounds have the advantage that their manufacture and impurity profile can be fully controlled.

The molecular weight of the radiopharmaceutical is suitably up to 5000 Daltons. Preferably, the molecular weight is in the range 150 to 3000 Daltons, most preferably 200 to 1500 Daltons, with 200 to 500 Daltons being especially preferred.

The synthetic compound exhibits biological targeting properties in the mammalian body in vivo, wherein imaging the uptake of the radioiodinated compound in the region of interest helps provide useful diagnostic information. Suitable such agents include blood flow imaging agents such as $^{123}$I-IMP or $^{123}$I-HIPDM, and kidney function imaging agents such as $^{123}$I-OIH. Preferably, the synthetic compound targets a biological receptor or a transporter affecting the function of an organ such as the brain, heart or kidney when administered to the mammalian body in vivo.

Synthetic targeting compounds which are most at risk of radiolysis are those which target biological receptors, enzymes or biological transporters in vivo. That is because such targeting compounds are normally best employed with the minimum amount of non-radioactive carrier compound present, since the non-radioactive compound is also biologically active, and is hence expected to compete with the $^{123}$-radiopharmaceutical for the biological site in vivo. At such no-carrier-added or high specific activity levels, and as the RAC will be fairly high the risk of radiolysis is increased. The stabilised compositions of the present invention are therefore particularly useful for radiopharmaceuticals wherein the synthetic targeting compound targets biological receptors, enzymes or biological transporters in vivo. Examples of such biological targets include the dopamine D-1 and D-2 receptors; the dopamine transporter in the brain; the cholinergic system; serotonin receptors; benzodiazepine receptors; the myocardial neuronal system; myocardial metabolism (beta oxidation); and metalloproteinases.

Examples of $^{123}$I-labelled synthetic compounds which target the dopamine D-2 receptor in the brain include $^{123}$I-Epidepride and $^{123}$I-IBZM, and are described by de Paulis [Curr. Pharm. Design, 9, 673-696 (2003)].

For the dopamine transporter, suitable agents include $^{123}$I-labelled tropanes, preferably $^{123}$I-CIT, $^{123}$I-CIT-FP (DaTSCAN™) and Altropane™, as described by Morgan and Nowotnik [Drug News Perspect., 12(3), 137-145 (1999)].

For the cholinergic system, imaging of the muscarinic acetylcholine system can be achieved with $^{123}$I-labelled quinuclidinyl benzilate (QNB) [Minoshima et al, Semin. Nucl. Med., 34(1), 70-82 (2004)].

For serotonin receptors, a suitable agent is an $^{123}$I-labelled 5-HT(2A) receptor antagonist such as R91150 [Eersels et al, J. Lab. Comp. Radiopharm., 48, 241-257 (2005)].

For the benzodiazepine receptor, a suitable agent is $^{123}$I-iomazenil [Minoshima et al, Semin. Nucl. Med., 34(1), 70-82 (2004)].

For the myocardial neuronal system, a suitable agent is $^{123}$I-MIBG [Wafelman et al, Appl. Rad. Isot., 45(10) 997-1007 (1994) and Kulkarni et al, Semin. Nucl. Med., 20(2), 119-129 (1990)]. For myocardial metabolism imaging, suitable agents include fatty acids, preferably BMIPP and IPPA [Corbett et al, Semin. Nucl. Med., 29(3), 237-258 (1999)].

When the synthetic compound comprises a benzamide, a preferred benzamide is IBZM. The corresponding preferred radiopharmaceutical is $^{123}$I-IBZM:

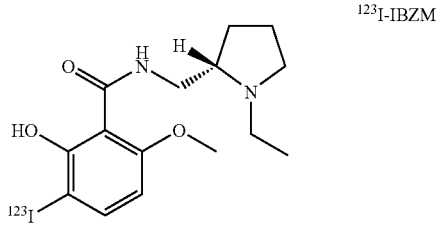

$^{123}$I-IBZM $^{123}$I-IBZM targets the dopamine D-2 receptor in the brain in vivo. The synthesis of $^{123}$I-IBZM is described by Bobeldijk et al [J. Lab. Comp. Radiopharm., 28, 1247-1256 (1990), Kung et al [J. Nucl. Med., 32, 339-342 (1991)] and Zea-Ponce et al [Nucl. Med. Biol., 26, 661-665 (1999)].

The synthetic compound is preferably a non-peptide. By the term "non-peptide" is meant a compound which does not comprise any peptide bonds, i.e. an amide bond between two amino acid residues.

$^{123}$I is a gamma-emitting radioisotope of iodine with a half-life of 13.2 hours. The $^{123}$I is preferably covalently attached to a phenyl group or a vinyl group of the synthetic compound, since C—I bonds where the carbon atom is sp$^2$ hybridised are more stable, and hence less prone to metabolism and deiodination both in vitro and in vivo than such bonds with sp or sp$^3$ hybridised carbon atoms. When the $^{123}$I-bonded phenyl group is also functionalised with one or more "activating groups", the compound is even more susceptible to deiodination, and hence the stabiliser compositions of the present invention are particularly useful. Examples of "activating groups" (X$^a$) are chosen from: —OH and —NH$_2$.

By the term "stabiliser" is meant a compound which inhibits degradation reactions, such as redox processes, by trapping highly-reactive free radicals, such as oxygen-containing free radicals arising from the radiolysis of water. The stabilisers of the present invention are suitably chosen from gentisic acid (i.e. 2,5-dihydroxybenzoic acid) and salts thereof with a biocompatible cation:

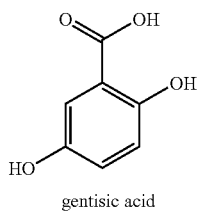

gentisic acid

The stabilisers of the present invention are present in an amount effective to stabilise the $^{123}$I-labelled synthetic compound against radiolysis. This means that the stabilisers are the principal means of stabilisation, and whilst other stabilisers could be present, the gentisic acid stabiliser is the predominant means of stabilisation, i.e. any additional stabiliser is present in an amount ineffective to stabilise on its own. Preferably, the gentisic acid stabiliser is the sole stabiliser present within the radiopharmaceutical composition. The gentisic acid stabilisers are suitably used at a concentration of 0.02 to 1.0% w/v concentration, preferably 0.03 to 0.4%, most preferably 0.05 to 0.2%, with 0.1% being especially preferred. Since increasing concentrations of gentisic acid will tend to lower the pH of the composition, adjustment of the pH or use of a buffer may be necessary at higher stabiliser concentrations.

By the term "biocompatible cation" is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium. Preferred stabilisers of the present invention are gentisic acid and sodium gentisate, which may be used alone or in combination.

The "biocompatible carrier medium" is a fluid, especially a liquid, in which the labelled synthetic compound is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. Such aqueous ethanol solutions may have a range of compositions, but 5-10% ethanol is preferred for the final composition. As indicated above, the pH of the biocompatible carrier medium for intravenous injection is suitably in the range 4.0 to 10.5. For the $^{123}$I-labelled radiopharmaceuticals of the present invention, the pH of the biocompatible carrier medium is suitably 4.5 to 8.5, preferably 4.6 to 8.0, most preferably 5.0 to 7.5.

When the $^{123}$I-labelled radiopharmaceutical is $^{123}$I-IBZM, the biocompatible carrier medium is preferably a mixed solvent solution of 5-10% ethanol with the remaining percentage being an aqueous buffer solution. The most preferred biocompatible carrier medium for $^{123}$I-IBZM is 8% ethanol and 92% aqueous buffer solution.

The radioactive concentration (RAC) of the $^{123}$I in the medium is suitably in the range 8 to 1000 MBq/cm$^3$. Preferably the RAC is in the range 18 to 500 MBq/cm$^3$. The higher the RAC, the greater the risk of radiolysis, and hence the greater the importance of the effective stabilisers of the present invention. In normal practice the RAC at the time of production is the highest, with radioactive decay meaning that the RAC is considerably lower by the time that formulation, testing, packaging and distribution to the customer have taken place.

The radiopharmaceutical compositions of the present invention are suitably supplied in a clinical grade syringe or a container which is provided with a seal which is suitable for single or multiple puncturing with a hypodermic needle (e.g. a crimped-on septum seal closure) whilst maintaining sterile integrity. Such containers may contain single doses (a "unit dose") or multiple patient doses. Suitable containers comprise a sealed vessel which permits maintenance of sterile integrity and/or radioactive safety, whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

When the radiopharmaceutical is supplied in a multiple dose container, preferred such containers comprise a single bulk vial (e.g. of 10 to 30 cm³ volume) which contains enough radiopharmaceutical for multiple patient doses. Unit patient doses can thus be withdrawn into clinical grade syringes at various time intervals during the viable lifetime of the bulk vial preparation to suit the clinical situation.

Radiopharmaceutical syringes designed to contain a single human dose, or "unit dose" and are therefore preferably a disposable or other syringe suitable for clinical use. Such syringes may optionally be provided with a syringe shield to protect the operator from radioactive dose. Suitable such radiopharmaceutical syringe shields are known in the art, and various designs are commercially available, and preferably comprise either lead or tungsten.

The radiopharmaceutical composition may optionally further comprise additional components such as an antimicrobial preservative, pH-adjusting agent or filler. By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the radiopharmaceutical composition is within acceptable limits (approximately pH 4.0 to 8.5) for human or mammalian administration. Suitable such pH-adjusting agents include pharmaceutically acceptable buffers, such as tricine, phosphate buffer or TRIS [i.e. tris(hydroxymethyl)aminomethane], and pharmaceutically acceptable bases such as sodium carbonate, sodium bicarbonate or mixtures thereof. For $^{123}$I-IBZM, a preferred buffer is phosphate buffer.

By the term "filler" is meant a pharmaceutically acceptable bulking agent which may facilitate material handling during product production. Suitable fillers include inorganic salts such as sodium chloride, and water soluble sugars or sugar alcohols such as sucrose, maltose, mannitol or trehalose.

Gentisic acid and salts thereof such as sodium gentisate are commercially available from a wide range of suppliers.

The radiopharmaceuticals of the present invention may be prepared under aseptic manufacture conditions to give the desired sterile, pyrogen-free product. The radiopharmaceuticals may also be prepared under non-sterile conditions, followed by terminal sterilisation using e.g. gamma-irradiation; autoclaving; dry heat; membrane filtration (sometimes called sterile filtration); or chemical treatment (e.g. with ethylene oxide). Preferably, the radiopharmaceutical compositions of the present invention are prepared as described in the third embodiment below. The $^{123}$I-labelled synthetic compounds are suitably prepared from precursors. The "precursor" suitably comprises a non-radioactive analogue of the synthetic compound having an element within its' chemical structure (Y) which is designed so that chemical reaction with a convenient chemical form of the $^{123}$I radioisotope occurs at Y, and can be conducted in the minimum number of steps (ideally a single step), and without the need for significant purification (ideally no further purification) to give the desired radioactive product. Such precursors are synthetic and can conveniently be obtained in good chemical purity. Suitable precursors and their preparation are described by Bolton, J. Lab. Comp. Radiopharm., 45, 485-528 (2002).

The source of the $^{123}$I is chosen from iodide ion or the iodonium ion (I⁺). Most preferably, the chemical form is iodide ion, which is typically converted to an electrophilic species by an oxidant during radiosynthesis.

The precursor is preferably provided as a composition which excludes the gentisic acid stabiliser. Preferred precursors are those wherein Y comprises a derivative which either undergoes electrophilic or nucleophilic iodination or undergoes condensation with a labelled aldehyde or ketone. Examples of the first category are:

(a) organometallic derivatives such as a trialkylstannane (e.g. trimethylstannyl or tributylstannyl), or a trialkylsilane (e.g. trimethylsilyl);

(b) aromatic rings activated towards electrophilic halogenation (e.g. phenols) and aromatic rings activated towards nucleophilic halogenation (e.g. aryl iodonium, aryl diazonium, nitroaryl).

Y suitably comprises: a non-radioactive precursor halogen atom such as an aryl iodide or bromide (to permit radioiodine exchange); an activated precursor aryl ring (e.g. a phenol group); an organometallic precursor compound (e.g. trialkyltin or trialkylsilyl); or an organic precursor such as triazenes or a good leaving group for nucleophilic substitution such as an iodonium salt. Methods of introducing $^{123}$I are described by Bolton [J. Lab. Comp. Radiopharm., 45, 485-528 (2002)]. Examples of suitable precursor aryl groups (Y) to which radioiodine can be attached are given below:

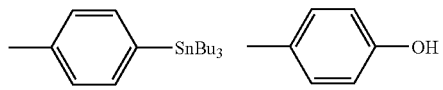

Both contain substituents which permit facile radioiodine substitution onto the aromatic ring. Alternative substituents containing radioactive iodine can be synthesised by direct iodination via radiohalogen exchange, e.g.

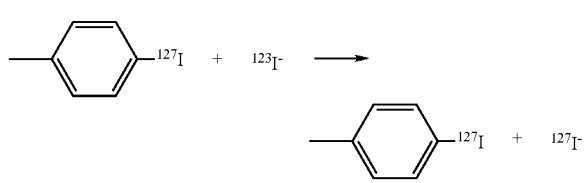

The "precursor" may optionally be covalently attached to a solid support matrix. In that way, the desired radiopharmaceutical forms in solution, whereas starting materials and impurities remain bound to the solid phase. A kit may therefore be employed which contains a cartridge which can be plugged into a suitably adapted automated synthesizer. The cartridge may contain, apart from the solid support-bound precursor, a column to remove unwanted radioactive iodide ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customer requirements for radioactive concentration, volumes, time of delivery etc. Conveniently, all components of the kit are disposable to minimise the possibility of contamination between runs and will be sterile and quality assured.

In a second aspect, the present invention provides a sterile stabiliser stock solution which comprises the gentisic acid stabiliser of the first embodiment in a biocompatible carrier medium in an environment from which oxygen gas has been removed.

The "biocompatible carrier medium" plus preferred aspects thereof are as described for the first embodiment.

By the phrase "environment from which oxygen gas has been removed" is meant that appropriate steps have been taken to keep the level of oxygen to the absolute minimum:

(a) when the stabiliser is in solution, oxygen gas has been displaced from the solution and steps are taken to ensure that the headspace gas over the solution is maintained oxygen-free. That is because the environment encompasses both the solution itself and the gas atmosphere that the solution comes into contact with;

(b) when the stabiliser solution is being prepared, oxygen-free solutions and reaction vessels are employed;

(c) when the stabiliser is in the solid state, an oxygen-free atmosphere is maintained over the solid.

The oxygen gas removal can be achieved by various methods known in the art, e.g. prolonged purging of the biocompatible carrier solution with a chemically unreactive gas so that any dissolved oxygen is displaced; freeze-thaw degassing of the biocompatible carrier solution with a chemically unreactive gas or lyophilisation where the atmosphere employed is such an unreactive gas.

The problematic brown colouration sometimes observed with prior art use of gentisic acid stabilisers is believed by the present inventors to be due to the quinhydrone complex formed upon oxidation of gentisic acid [T. J. Holmes et al, J. Org. Chem., 49, 4736-4738 (1984)].

By the term "chemically unreactive gas" is meant a gas which would be used in chemistry to provide an "inert atmosphere" as is known in the art. Such a gas does not undergo facile oxidation or reduction reactions (e.g. as would oxygen and hydrogen respectively), or other chemical reactions with organic compounds (as would e.g. chlorine), and is hence compatible with a wide range of synthetic compounds without reacting with the synthetic compound, even on prolonged storage over many hours or even weeks in contact with the gas. Suitable such gases include nitrogen or the inert gases such as helium or argon. Preferably the chemically unreactive gas is nitrogen or argon. Most preferably, the chemically unreactive gas is heavier than air, which maintains a blanket over the stabiliser composition. Hence, a preferred chemically unreactive gas is argon. In order to ensure that ingress of oxygen gas into the de-oxygenated solution does not occur, the headspace gas over the stabiliser is either maintained under a positive pressure of the unreactive gas, or the stabiliser is kept in a gas-tight container (as described above), with the headspace gas being a chemically unreactive gas. Pharmaceutical grade chemically unreactive gases are commercially available.

A preferred biocompatible carrier medium for the stabiliser stock solution comprises an aqueous solution at a pH suitable for intravenous administration. A preferred such aqueous solution is a buffer solution, most preferably phosphate buffer. When the radiopharmaceutical is $^{123}$I-IBZM, the pH of the buffered stock solution is suitably pH 5 to 8, preferably 5.4 to 7, most preferably 5.7 to 6.3. As noted above, gentisic acid solutions tend to suffer from discoloration problems. It has now been found that sterile gentisic acid solutions in aqueous buffer can be prepared which do not discolour even on storage for more than a year, as long as appropriate steps are taken to minimise the presence of oxygen gas in the environment. The stock solutions may be prepared under non-sterile conditions, followed by terminal sterilisation using e.g. gamma-irradiation, autoclaving, dry heat or chemical treatment (e.g. with ethylene oxide). Alternatively, the stock solutions may be prepared under aseptic manufacture conditions to give the desired sterile, pyrogen-free product. Preferably the sterile stock solutions are prepared by terminal sterilisation, most preferably by autoclaving. Such autoclaving involves steam heating at over 121° C., so represents stress conditions wherein unwanted chemical reactions might be expected. The alternative stabiliser ascorbic acid does not withstand such heat sterilisation in buffer solution. It is therefore surprising that the lack of discolouration for gentisic acid can be maintained under such conditions. In contrast, if oxygen is not excluded and gentisic acid solutions are subjected to autoclave sterilisation, visible discolouration does occur, giving brown solutions which darken further on standing.

The stock solutions are employed in a suitable sealed container, as described for the radiopharmaceutical above. The gentisic acid stock solution in an oxygen-free medium is therefore a much more useful, and more widely applicable stabiliser for $^{123}$I-labelled radiopharmaceuticals, since it can be used without discoloration problems. The sterile stabiliser solutions of the present invention are therefore colourless or almost colourless, since they lack oxidation products of gentisic acid, in particular quinhydrones. After preparation, the gentisic acid stock solution is preferably stored in the dark at 2 to 8° C., since those precautions also help to prevent discoloration.

The non-radioactive stock solution has the advantage that it can be prepared, assayed and quality-controlled in advance and kept in a sterile state so that it can used in the manufacture of different batches of $^{123}$I-radiopharmaceutical at different times and/or days. This saves manufacturing time in each batch run, which is important because the product in question has a half-life of 13.2 hours. The concentration of the gentisic acid in the stock solution can be assayed by standard methods, such as HPLC.

In a third aspect, the present invention provides a method of preparation of the stabilised radiopharmaceutical composition of the first embodiment, which comprises mixing the following sterile solutions:

(i) the $^{123}$I-labelled synthetic compound of the first embodiment in a biocompatible carrier medium;

(ii) an aliquot of the gentisic acid stock solution of the second embodiment;

wherein the radioactive concentration of the $^{123}$I radiopharmaceutical product in the resulting mixed medium is in the range 8 to 1000 MBq/cm$^3$ and the pH of the biocompatible carrier medium in the resulting radiopharmaceutical composition is in the range 4.5 to 8.5.

The "biocompatible carrier medium" for (i) and (ii) may be the same or different, and is as described for the first and second embodiments (above), including the preferred aspects thereof. Thus, in step (i), the medium could be 100% ethanol, which is diluted with an aqueous buffer in step (ii) to give a final aqueous ethanolic buffer composition. When the radiopharmaceutical is $^{123}$I-IBZM, the solvent for solution (i) is preferably ethanol, and the solvent for solution (ii) preferably phosphate buffer, with a final composition having an ethanol content of 5-10%. Preferred embodiments of the stabiliser are as described for the first embodiment above. Other aspects of the stabiliser stock solution (ii), including suitable concentrations of stabiliser are as described for the second embodiment.

It should be noted that the $^{123}$I-labelled synthetic compound is suitably already prepared, and preferably purified to remove impurities (e.g. excess reactants), before mixing with the gentisic acid stabiliser takes place. That is because methods for the introduction of $^{123}$I from iodide as the source of radioisotope almost always involve the use of an oxidising agent. Gentisic acid is a reducing agent, and would hence interfere with the radiolabelling, or potentially even generate undesirable redox reaction products and discolouration.

The timing of the introduction of the stabiliser should be such that the mixing takes place as soon as possible after the production of the $^{123}$I-labelled compound, since the longer the $^{123}$I-labelled synthetic compound is in solution in the absence of a stabiliser, the greater the risk of radiolysis. If the $^{123}$I-labelled compound has been purified and has been dissolved in a biocompatible solvent (e.g. ethanol), this may be less crucial, since the purified compound in a 100% organic solvent medium is expected to be relatively stable.

It is preferred that the solution of stabiliser [solution (ii)] is provided in an environment from which oxygen gas has been excluded. Methods for the exclusion of oxygen gas are described in the second embodiment above. Solution (i) and the radiopharmaceutical product may optionally also be maintained in an environment from which oxygen gas has been excluded, but this is only really important for solution (ii).

In a fourth aspect the present invention provides the use of gentisic acid or a salt thereof with a biocompatible cation as a stabiliser to stabilise against radiolysis an $^{123}$I-labelled synthetic compound in solution in an aqueous biocompatible carrier medium as defined in the first embodiment, wherein the radioactive concentration of the $^{123}$I in the medium is in the range 8 to 1000 MBq/cm$^3$ and the pH of said biocompatible carrier medium is in the range 4.5 to 8.5.

Preferred aspects of the stabiliser, synthetic compound and biocompatible carrier medium are as described for the first embodiment (above).

This use is particularly valuable for aqueous solutions which are in a form suitable for human administration as a radiopharmaceutical, i.e. are in sterile form as described above.

The invention is illustrated by the non-limiting Examples detailed below. $^{123}$I-IBZM stabilised with ascorbic acid is commercially available from GE Healthcare, Netherlands. Example 1 compares the stabilisation of $^{123}$I-IBZM with gentisic acid compared with the prior art stabiliser ascorbic acid. This shows that the principal radiochemical impurity (i.e. free $^{123}$I-iodide) in the radiopharmaceutical preparation is almost halved from ca. 4 to 5% to 2 to 3% at the moment of use when gentisic acid is employed. Whilst $^{123}$I-iodide does not cross the blood-brain-barrier, this improvement reduces the level of radiochemical impurity administered to the patient.

Example 2 shows that gentisic acid is an effective stabiliser over the concentration range 0.06 to 0.34% w/v, with very similar results in the range 0.13 to 0.34% w/v. Example 3 shows that a gentisic acid stock solution sterilised in an autoclave (i.e. steam) sterilisation step at 121° C. is still an effective stabiliser for $^{123}$I-IBZM. Example 4 and FIG. 1 shows that, for the stabilisation of $^{123}$I-IBZM, there is a concentration of gentisic acid stabiliser above which little or no additional stabilisation benefit is obtained. Example 5 shows that gentisic acid is also effective to stabilise $^{123}$-MIBG, and is effective at much lower concentrations than benzyl alcohol.

EXAMPLE 1

Gentisic Acid (GA) vs Ascorbic Acid (AA) Stabilisation of $^{123}$I-IBZM $^{123}$I-IBZM was prepared by the method of Bobeldijk et al [J. Lab. Comp. Radiopharm., 28, 1247-1256 (1990)]. A small series of $^{123}$I-IBZM solutions was prepared: to each vial 200 μl of $^{123}$I-IBZM in EtOH (925 MBq/cm$^3$) was added and subsequently 2.3 ml of aqueous phosphate buffer solution optionally containing a stabiliser, in such a way that the resulting ethanol content was 8% and the radioactive concentration at calibration time was 74 MBq/cm$^3$ (2 mCi/ml).

The vials were stored at ambient temperature and the radiochemical purity (RCP) was determined by thin layer chromatography (TLC) at the time of dilution with phosphate buffer and at 24 and 48 hours afterwards. The results are shown in Table 1:

TABLE 1

Stabilisation of $^{123}$I-IBZM with AA and GA.

| Vial | Concentration of Stabiliser in Buffer | pH | RCP (% IBZM) at time (hours) | | |
|---|---|---|---|---|---|
| | | | 0 h* | 24 h | 48 h |
| C (185 MBq) | 0.05% GA | 5.7 | 99.0* | 98.2 | 97.7 |
| D (111 MBq) | 0.05% AA (prior art) | 5.7 | 99.0* | 95.0 | 93.8 | where: AA = ascorbic acid and GA = gentisic acid.
*The RCP on day of production (EOS) is measured at a random vial within a batch, and is assumed to be representative. It has been demonstrated that the RCP at EOS does not differ significantly between various compositions.

EXAMPLE 2

Effect of Concentration of Gentisic Acid on the Stabilisation of $^{123}$I-IBZM $^{123}$I IBZM in EtOH was prepared as per Example 1. A small series of $^{123}$I-IBZM solutions was prepared: to each vial 120 μl of $^{123}$I-IBZM in EtOH (925 MBq/cm$^3$) was added and subsequently 1.38 ml of aqueous phosphate buffer solution containing a stabiliser, in such a way that the resulting ethanol content was 8% and the radioactive concentration at calibration time was 74 MBq/cm$^3$ (2 mCi/ml). The vials were stored at ambient temperature and the RCP was determined at 24 and 46 hours after dilution with phosphate buffer. The results are given in Table 2:

TABLE 2

Effect of Concentration of GA on the Stabilisation of $^{123}$I-IBZM.

| Vial | Concentration of Stabiliser in Buffer | Radioactive Concentration (at calibration time) | pH | RCP (% IBZM) at time | |
|---|---|---|---|---|---|
| | | | | 24 h | 46 h |
| Q | 0.05% AA$ | 20 MBq in 0.25 ml | 5.8 | 95.5 | 95.3 |
| A | 0.05% AA$ | 111 MBq in 1.5 ml | 5.8 | 96.3 | 96.0 |
| B | 0.06% GA | 111 MBq in 1.5 ml | 6.1 | 97.5 | 97.3 |
| C | 0.13% GA | 111 MBq in 1.5 ml | 6.2 | 98.0 | 97.5 |
| D | 0.20% GA | 111 MBq in 1.5 ml | 6.1 | 98.1 | 97.8 |
| E | 0.34% GA | 111 MBq in 1.5 ml | 6.1 | 98.0 | 97.9 | where: AA = ascorbic acid and GA = gentisic acid.
$the stock solution of AA was not sterilised.

EXAMPLE 3

Effect of Sterilised Stock Solutions on the Stabilisation of $^{123}$I-IBZM with Gentisic Acid Stock solutions of the stabilisers shown were prepared, purged with argon gas and then sealed under argon in a septum-sealed vial with a Teflon™ coated rubber stopper.

The solutions were sterilised by autoclaving for 15 minutes at 121° C., and then allowed to cool to ambient temperature before use.

A small series of $^{123}$I-IBZM solutions was prepared: to each vial $^{123}$I-IBZM in EtOH (925 MBq/cm$^3$) was added and subsequently an aqueous phosphate buffer solution containing a stabiliser as specified in Table 3 (below), in such a way that the resulting ethanol content was 8% and the radioactive concentration at calibration time was 74 MBq/cm$^3$ (2 mCi/ml). The RCP of each vial was determined 3 hours after preparation and after storage at room temperature for 51 hours.

TABLE 3

| Vial | Activity (mCi) | Concentration of Stabiliser in Buffer | pH | RCP (% IBZM) at time | |
|---|---|---|---|---|---|
| | | | | 3 h | 51 h |
| C | 3.75 | 0.05% GA | 5.8 | 99.1 | 97.5 |
| D | 3.75 | 0.10% GA | 5.6 | 99.2 | 97.7 |
| Q | 0.5 | 0.05% AA | 5.7 | 98.6 | 94.2 |
| S | 5.0 | 0.05% AA | 5.7 | 98.6 | 93.0 | where: AA = ascorbic acid and GA = gentisic acid.

EXAMPLE 4

Effect of Concentration of Gentisic Acid in the Stock Solution on the Stabilisation of $^{123}$I-IBZM Step (a): Gentisic Acid Solutions.

A phosphate buffer solution (300 ml) was divided into 6 vials each of 50 ml with various amounts of gentisic acid, corresponding to w/v concentrations of 0%, 0.024%, 0.050%, 0.10%, 0.20% and 0.39%. The pH was checked, and if necessary adjusted by the addition of NaOH to obtain a pH of 5.8 (±0.1). The vials were stoppered with Teflon™ coated rubber stoppers and sterilised for 15 min at 121° C.

Step (b): $^{123}$I-IBZM Solutions.

An ethanolic solution of $^{123}$I-IBZM (activity concentration at REF: 925 MBq/ml (25 mCi/ml)) was divided over 6 vials and into each was added an aliquot of the 6 gentisic acid buffer solutions from step (a) to obtain a final solution with a total activity content of 185 MBq (5 mCi), at a RAC of 74 MBq/ml (2 mCi/ml) and an ethanol content of 8%. The vials were stoppered with a Teflon™ coated rubber stopper and stored at room temperature. The RCP was measured at various time points after EOS. Representative results are shown in FIG. 1.

EXAMPLE 5

Stabilizing Effect of Gentisic Acid on $^{123}$I-mIBG in Phosphate Buffer

Two series of 5 vials of $^{123}$I-mIBG solutions were prepared: to each vial an aliquot of 0.5 cm$^3$ of freshly prepared $^{123}$I-mIBG in (stabiliser-free) Phosphate buffer (360 MBq/cm$^3$) was added and subsequently an aliquot of 2.0 cm$^3$ of an aqueous phosphate buffer solution containing a stabiliser as specified in Table 4 (below), followed by mixing. The final mixtures were not heat sterilized. The total activity per vial was 185 MBq with an RAC of 74 MBq/ml. The specific activity was 992 GBq/g mIBG base. Vials A1 to E1 were stored at 40° C. and vials A2 to E2 at 20° C. The RCP was determined at the EOS (end of synthesis) and at 3, 20 and 45 hours thereafter. The results are given in Table 5:

TABLE 4

| Phosphate buffer solutions (pH 6) | |
|---|---|
| Buffer | Concentration of Stabiliser |
| A | 1% benzyl alcohol |
| B | No stabiliser |
| C | 0.03% GA |
| D | 0.06% GA |
| E | 0.13% GA |

TABLE 5

Stabilisation of $^{123}$I-MIBG with Benzyl alcohol and Gentisic acid

| Vial | Concentration of Stabiliser in Buffer | RCP (% mIBG) at time (hours) Storage at 20° C. | | | |
|---|---|---|---|---|---|
| | | EOS | EOS + 3 h | EOS + 20 h | EOS + 45 h |
| A2 | 0.8% Benzyl alcohol | 99.7 | 99.5 | 98.8 | 98.1 |
| B2 | no stabiliser | 99.6 | 98.8 | 95.6 | 93.2 |
| C2 | 0.024% GA | 99.7 | 99.5 | 98.2 | 97.6 |
| D2 | 0.048% GA | 99.7 | 99.5 | 98.7 | 98.3 |
| E2 | 0.104% GA | 99.7 | 99.5 | 99.2 | 99.0 |

| Vial | Concentration of Stabiliser in Buffer | RCP (% mIBG) at time (hours) Storage at 40° C. | | | |
|---|---|---|---|---|---|
| | | EOS | EOS + 3 h | EOS + 20 h | EOS + 45 h |
| A1 | 0.8% Benzyl alcohol | 99.7 | 99.5 | 98.6 | 98.2 |
| B1 | no stabiliser | 99.6 | 98.3 | 94.0 | 92.0 |
| C1 | 0.024% GA | 99.7 | 99.3 | 98.1 | 97.2 |
| D1 | 0.048% GA | 99.7 | 99.5 | 98.6 | 98.3 |
| E1 | 0.104% GA | 99.7 | 99.6 | 99.0 | 98.9 |

The invention claimed is:

1. A stabilised radiopharmaceutical composition which comprises:
   (i) a synthetic, non-peptide compound which targets a site within the mammalian body when administered in vivo which is labelled with $^{123}$I, where the $^{123}$I is covalently attached to a phenyl group or a vinyl group of the synthetic compound;
   (ii) a stabiliser which comprises gentisic acid or a salt thereof with a biocompatible cation in an amount effective to stabilise said $^{123}$I-labelled synthetic compound against radiolysis;
   (iii) an aqueous biocompatible carrier medium;
   wherein the radioactive concentration of the $^{123}$I in the medium is in the range 8 to 1000 MBq/cm$^3$ and the pH of the biocompatible carrier medium is in the range 4.5 to 8.5;
   with the proviso that when the synthetic compound which targets a site within the mammalian body is meta-iodobenzylguanidine, the pH of the biocompatible carrier medium is in the range 5.0 to 8.5.

2. The composition of claim 1, wherein the synthetic compound targets the brain or the heart when administered to the mammalian body in vivo.

3. The composition of claim 1, wherein the synthetic compound targets a biological receptor, enzyme or biological transporter in vivo.

4. The composition of claim 3, where the synthetic compound is IBZM.

5. The composition of claim 1, where the phenyl group is substituted with one or more activating groups ($X^a$) where $X^a$ is chosen from: —OH and —$NH_2$.

6. The composition of claim 1, where the sole stabiliser present is gentisic acid or a salt thereof with a biocompatible cation.

7. The composition of claim 1, where the stabiliser comprises gentisic acid or sodium gentisate.

8. The composition of claim 1, where the biocompatible medium comprises an aqueous solution.

9. The composition of claim 1, where the concentration of the stabiliser in the medium is in the range 0.02 to 1.0% w/v.

10. A sterile stabiliser stock solution which comprises a stabiliser which comprises gentisic acid or a salt thereof with a biocompatible cation in a biocompatible carrier medium in an environment from which oxygen gas has been removed.

11. The stock solution of claim 10, which is sterilised by a heat sterilisation process.

12. The stock solution of claim 10, which is colourless.

13. A method of preparation of a stabilised radiopharmaceutical composition of claim 1, which comprises the step of mixing:
  (i) a sterile solution of a biocompatible carrier medium which comprises a synthetic compound which is labeled with $^{123}I$ and which targets a site within the mammalian body when administered in vivo; and
  (ii) a sterile solution of a biocompatible carrier medium comprising an aliquot of gentisic acid or a salt thereof with a biocompatible cation in an amount effective to stabilise said $^{123}I$-labelled synthetic compound against radiolysis;
  wherein said mixing step is performed in an environment from which oxygen has been removed and wherein the radioactive concentration of the $^{123}I$ radiopharmaceutical product in the resulting mixed medium is in the range 8 to 1000 $MBq/cm^3$ and the pH of the biocompatible carrier medium in the resulting radiopharmaceutical composition is in the range 4.5 to 8.5.

14. A method of stabilizing an $^{123}I$-labelled synthetic compound in solution in an aqueous biocompatible carrier medium, wherein the radioactive concentration of the $^{123}I$ in the medium is in the range 8 to 1000 $MBq/cm^3$ and the pH of said biocompatible carrier medium is in the range 4.5 to 8.5,
  wherein said method comprises the addition of gentisic acid or a salt thereof with a biocompatible cation to said solution;
  and wherein said compound is a synthetic, non-peptide compound which targets a site within the mammalian body when administered in vivo which is labelled with $^{123}I$, where the $^{123}I$ is covalently attached to a phenyl group or a vinyl group of the synthetic compound.

15. The method of claim 14, where the solution is in a form suitable for human administration as a radiopharmaceutical.

* * * * *